(12) United States Patent
Finkel et al.

(10) Patent No.: US 6,682,728 B1
(45) Date of Patent: Jan. 27, 2004

(54) EFFICIENT AND SELECTIVE ADENOVIRAL-MEDIATED GENE TRANSFER INTO VASCULAR NEOINTIMA

(75) Inventors: Toren Finkel, Bethesda, MD (US); Raul G. Guzman, Rockville, MD (US); Ronald G. Crystal, Potomac, MD (US); Stephen E. Epstein, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1,826 days.

(21) Appl. No.: 08/136,113

(22) Filed: Oct. 13, 1993

(51) Int. Cl.[7] ............................ A01N 63/00; A61K 48/00
(52) U.S. Cl. ................... 424/93.2; 424/93.6; 435/320.1
(58) Field of Search ........................ 514/44; 435/172.3, 435/320.1; 935/62; 424/93.2, 6

(56) References Cited

U.S. PATENT DOCUMENTS 5,304,122 A * 4/1994 Schwartz et al. ............. 604/53
5,328,470 A * 7/1994 Nabel et al. ................. 604/101

FOREIGN PATENT DOCUMENTS

EP 0 494 776 A1 7/1992

OTHER PUBLICATIONS

Mulligan et al, Science, vol. 260, May 14, 1993, pp. 926–932.*
Ledley, Human Gene Therapy 2:77–83 (1991).*
Takeshita et al, Circulation, Supp. I, vol. 86 No. 4, (Oct. 1992), Abstract Nos. 3179 and 0903.*
T. Ohno et al. (1994) Science 265:781–784.*
Thierry Ragot et al., "Efficient Adenovirus–Mediated Transfer of a Human Minidystrophin Gene to Skeletal Muscle of mdx Mice," *Nature*, 361:647–650 (Feb. 18, 1993).
Sadatoshi Biro et al., "Inhibitory Effects of Antisense Oligodeoxynucleotides Targeting c–myc mRNA on Smooth Muscle Cell Proliferation and Migration," *Proc. Natl. Acad. Sci., USA*, 90:654–658 (Jan. 1993).
John E. Willard et al., "Recombinant Adenovirus is an Efficient Vector for In Vivo Gene Transfer and Can be Preferentially Directed at Vascular Endothelium of Smooth Muscle Cells," *Abstracts From the 65th Scientific Sessions*, 86(4):I–473 (Oct. 1992).
Michael Simons et al., "Antisense c–myb Oligonucleotides Inhibit Intimal Arterial Smooth Muscle Cell Accumulation In Vivo," *Nature*, 359:67–70 (Sep. 3, 1992).
Ward Casscells et al., "Elimination of Smooth Muscle Cells In Experimental Restenosis: Targeting of Fibroblast Growth Factor Receptors," *Proc. Natl. Acad. Sci. USA*, 89:7159–7163 (Aug. 1992).
Béatrice Quantin et al., "Adenovirus as an Expression Vector in Muscle Cells In Vivo," *Proc. Natl. Acad. Sci., USA*, 89:2581–2584 (Apr. 1992).
Edith Speir et al., "Inhibition of Smooth Muscle Cell Proliferation by an Antisense Oligodeoxynucleotide Targeting the Messenger RNA Encoding Proliferating Cell Nuclear Antigen," *Circulation*, 86:538–547 (1992).
Stephen E. Epstein et al., "Cytotoxic Effects of a Recombinant Chimeric Toxin on Rapidly Proliferating Vascular Smooth Muscle Cells," *Circulation*, 84:778–787 (1991).
Haj–Ahmad and Graham, "Development of a Helper–Independent Human Adenovirus Vector and its Use in the Transfer of the Herpes Simplex Virus Thymidine Kinase Gene," *Journal of Virology* vol. 57, Jan. 1986, p. 267–274.

* cited by examiner

*Primary Examiner*—Deborah Crouch
(74) *Attorney, Agent, or Firm*—Leydig, Voit & Mayer, Ltd.

(57) ABSTRACT

The present invention provides a method of selectively expressing DNA in neointimal cells in an injured blood vessel of a subject comprising administering a replication-deficient recombinant adenovirus which functionally encodes the DNA to the blood vessel at the site of injury, such that the adenovirus remains at the site of injury for a time sufficient for the adenovirus to selectively infect neointimal cells and thereby selectively express the DNA in neointimal cells. In particular, the invention provides administering a replication-deficient recombinant adenovirus which functionally encodes a DNA encoding a protein or an antisense ribonucleic acid. This method can be used to treat restenosis and, relatedly, prevent neointimal cell proliferation.

20 Claims, 1 Drawing Sheet

EFFICIENT AND SELECTIVE ADENOVIRAL-MEDIATED GENE TRANSFER INTO VASCULAR NEOINTIMA

BACKGROUND OF THE INVENTION

1. Field of the Invention

The present invention relates to a method of delivering DNA to neointimal cells in injured blood vessels. In particular is provided a method of decreasing or inhibiting the proliferation of neointimal cells by delivering DNA that causes the decrease or inhibition of proliferation of neointimal cells, using replication-deficient recombinant adenoviral vectors, thus treating restenosis.

2. Background Art

The smooth muscle cell (SMC) proliferation associated with arterial injury remains a major obstacle to the long-term success of coronary angioplasty. The injury activates medial SMCs, which begin to migrate and proliferate to form a neointima. Angioplasty failure rates of 25% to 50% within six months have been reported and confirmed by several authors (1–5). Previous attempts to modulate this cellular proliferation have included various mechanical and pharmacologic therapies, which have been the subject of several reviews (6–9). More recently, many efforts have been directed against various growth factors, their receptors, or cellular proto-oncogenes thought to play an important role in SMC proliferation (10–19). Although several of these methods have shown encouraging in vitro, and more recently, in vivo results, all approaches have both practical and theoretical drawbacks. Hence, while one or more of these therapeutic strategies may ultimately show clinical efficacy, the need for more powerful and specific approaches is compelling.

Gene therapeutic techniques offer the promise of efficiently transferring genes, whose products may convey therapeutic benefit, to specific groups of cells. Previous efforts to directly transduce arterial segments in vivo have used liposomal or retroviral methods to transfer marker genes into endothelial or SMCs (20–24). The feasibility of such efforts, however, has been limited by a low transfection efficiency. In in vivo models, estimates of gene transfer into arterial segments range from fewer than 1 in 10,000 cells transduced with retroviral methods (24) to fewer than 1 in 1,000 cells using liposomes.

Replication deficient recombinant adenoviral vectors have previously been shown to be efficient for transferring exogenous genes to a wide variety of cells in vivo (25–36). Such vectors can be manipulated so as to encode for recombinant gene products up to 7.5 kilobases (kb) in length (37). The recombinant virus can be propagated in certain mammalian cell lines that serve to complement the growth of replication detective adenovirus. Additionally, transduction by adenovirus, as opposed to retrovirus, does not depend on active replication of the host cell (37,38).

The present invention provides for the use of adenoviral vectors for selective and efficient expression of DNA in neointimal cells at the site of an injury. This expression can be utilized as a much needed means to treat restenosis.

SUMMARY OF THE INVENTION

The present invention provides a method of selectively expressing DNA in neointimal cells in an injured blood vessel of a subject comprising administering a replication-deficient recombinant adenovirus which functionally encodes the DNA to the blood vessel at the site of injury, such that the adenovirus remains at the site of injury for a time sufficient for the adenovirus to selectively infect neointimal cells and thereby selectively express the DNA in neointimal cells. In particular, the invention provides administering a replication-deficient recombinant adenovirus which functionally encodes a DNA encoding a protein or an antisense ribonucleic acid.

The instant invention also provides a method of treating restenosis in an injured blood vessel of a subject comprising administering to the blood vessel a replication-deficient recombinant adenovirus which functionally encodes a DNA which can decrease the proliferation of neointimal cells, such that the adenovirus remains at the site of injury for a time sufficient for the adenovirus to selectively infect and express the DNA in neointimal cells, thereby decreasing or inhibiting the proliferation of neointimal cells and treating restenosis.

Additionally, the present invention provides a method of preventing neointimal cell proliferation in an injured blood vessel of a subject comprising administering to the blood vessel a replication-deficient recombinant adenovirus which functionally encodes a DNA which can decrease the proliferation of neointimal cells, such that the adenovirus remains at the site of injury for a time sufficient for the adenovirus to selectively infect and express the DNA in neointimal cells, thereby preventing the proliferation of neointimal cells. Also provided is the use of this method of preventing neointimal cell proliferation to treat primary atherosclerosis.

The present invention further provides a method of screening DNA for the ability to inhibit proliferation of or to have cytotoxic effects on neointimal cells comprising administering to an injured blood vessel in a subject at the site of injury a replication-deficient adenovirus which functionally encodes the DNA, for a time sufficient for the adenovirus to selectively infect neointimal cells; and detecting inhibition of proliferation of or toxicity to the neointimal cells, such inhibition or toxicity indicating a DNA having the ability to inhibit proliferation of or to have cytotoxic effects on neointimal cells.

DESCRIPTION OF THE PREFERRED EMBODIMENTS

Figure 1:
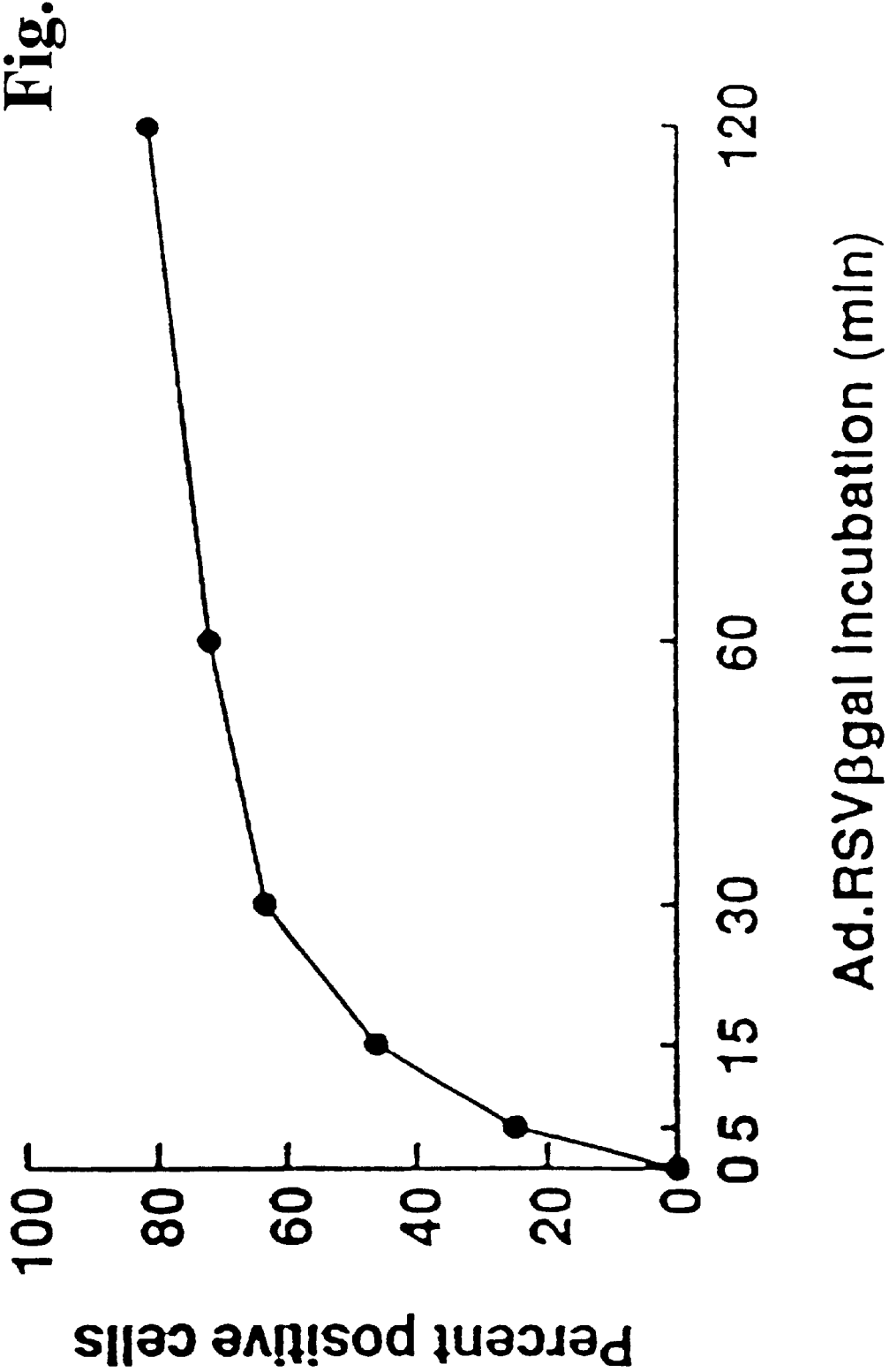
FIG. 1 shows time dependence of adenovirus-mediated gene transfer into cultured vascular SMCs. Quiescent SMCs were exposed to media containing Ad.RSVβgal for varying time intervals as described in the text and percent of cells that are nuclear dominant blue staining are plotted as a function of time viral incubation. Five hundred cells were counted in duplicate flasks that had been stained for β-gal activity. Averages from duplicate flasks varied less than 5% from the mean. Data shown are from one experiment but are representative of 3 different experiments.

The present invention may be understood more readily by reference to the following detailed description of specific embodiments and the Examples and Figures included therein.

The present invention provides a method of selectively expressing DNA in neointimal cells in an injured blood vessel of a subject comprising administering a replication-deficient recombinant adenovirus which functionally encodes the DNA to the blood vessel at the site of injury, such that the adenovirus remains at the site of injury for a time sufficient for the adenovirus to selectively infect neointimal cells and thereby selectively express the DNA in neointimal cells. Any blood vessel injured sufficiently to cause neointimal cell formation is contemplated as "an injured blood vessel" herein.

The administration step is preferably performed at least 4 days after the blood vessel is injured, and more preferably, at least about 7 or at least about 12 days following injury. By administration "at the site of injury" is meant such that the adenovirus contacts the injured walls of the blood vessel, including the neointimal cells formed. Preferably, the adenovirus is administered, such that the adenovirus remains at the site of injury, i.e., in contact with the region of the vessel wall having neointimal cells, a sufficient time for the adenovirus to selectively infect neointimal cells. A preferable amount of time for contact of adenovirus with neointimal cells is from about 15 minutes to about 60 minutes.

The exact method of administration can affect how the virus is placed in contact with neointimal cells. For example, one known means of administering to the bloodstream is by use of commercially available catheters for dwelling solutions. Delivery of such solutions by catheter is standard and known in the art (see e.g., 50). When using such catheters, the catheter is placed precisely at the site of injury within the blood vessel to allow for the adenovirus to selectively infect the neointimal cells. Other administration means, for example, as described herein, can be used. Therefore, any administration method, for any amount of time that causes the recombinant to contact neointimal cells for a time sufficient to selectively infect the neointimal cells is contemplated herein.

By "selectively" infecting neointimal cells is meant that the adenovirus infects neointimal cells while only minimally, if at all, infecting non-neointimal cells. Specific examples of such selective infection are provided herein. In particular, it is meant that primarily neointimal cells are infected. Generally, minimal, e.g., less than about 10% and usually less than about 1%, infection occurs in surrounding endothelial cells or medial SMCs and in distal organs, such as the heart, brain or liver. By "selective infection" is also meant that at least 20% neointimal cells be infected, and preferably at least 50%.

"Expressing DNA", as used herein, includes the transcription of the DNA into a ribonucleic acid if an antisense construct is used. "Expressing DNA" also includes both transcription of DNA into an mRNA and translation of the mRNA into protein when an expressed protein is desired. DNA can be genomic DNA or complementary DNA (cDNA). Therefore, "selectively expressing DNA in neointimal cells" is meant that the protein or antisense RNA is produced selectively in the neointimal cells in the blood vessel.

A "replication-deficient recombinant adenovirus, which functionally encodes the DNA", includes any adenovirus incapable of replication, many of which are known in the art, into which has been cloned a DNA sequence to be expressed after infection of a cell by the adenovirus. By "functionally encodes" is meant that the DNA is capable, for example, of transcription and translation into the encoded protein or capable of transcription into an antisense RNA, in the infected cells. Thus, the DNA has any necessary sequences for expression (i.e., promoter, etc.).

Replication deficient recombinant adenoviruses containing the DNA of choice can be constructed by standard molecular techniques. For example, this invention demonstrates the use of a cotransfection system with the plasmid pJM17, which was first described in 1988. In this method, the gene (cDNA) of interest is first cloned into a shuttle vector, in which the cDNA, of interest, is flanked by adenoviral sequences. This shuttle plasmid is then cotransfected with the pJM17 plasmid into 293 cells. The pJM17 plasmid contains the entire Ad5 DNA molecule, but contains an insert in the E1 region of the virus resulting in a viral genome that exceeds the packaging constraints of adenoviral capsids. Recombination of the shuttle plasmid with pJM17 can result in a recombinant virus which can now be packaged as long as the cDNA is less than a certain size (usually $\leq 2$ kb). Such recombinant viruses can be detected as plaques on a lawn of 293 cells. Viral particles can subsequently be amplified so as to be produced in large amounts (49).

As noted above, a DNA encoded by an adenovirus herein can encode a protein or an antisense ribonucleic acid. DNA encoding a protein can be selected according to the protein desired for expression in neointimal cells, for example, for therapeutic purposes. A DNA encoding an antisense RNA can be selected according to a protein desirable to inhibit or decrease in neointimal cells, by providing an RNA that will selectively bind to the cellular mRNA encoding such protein.

Relatedly, the present invention also includes a method of treating restenosis in an injured blood vessel of a subject comprising administering to the blood vessel a replication-deficient recombinant adenovirus which functionally encodes a DNA which can decrease the proliferation of neointimal cells, such that the adenovirus remains at the site of injury for a time sufficient for the adenovirus to selectively infect and express the DNA in neointimal cells, thereby decreasing or inhibiting the proliferation of neointimal cells and treating restenosis. A DNA which can decrease the proliferation of neointimal cells can encode either a protein the provision of which to the neointimal cells will cause a decrease in proliferation of the neointimal cells, or an antisense RNA corresponding to a cellular protein, the inhibition or decrease of which in the neointimal cells will cause a decrease in the proliferation of the neointimal cells. Many examples of such proteins are known, and it can include the herpes virus thymidine kinase gene, the dominant-negative ras gene product, and nitric oxide synthase, all of which are known in the art. Examples of useful antisense RNA include c-myc, c-myb, CDC2 and PCNA (10–18). Specifically, a DNA that, when expressed, is inhibitory or cytotoxic to the neointimal cells can be used to decrease proliferation of neointimal cells.

The present invention further provides a related method of preventing neointimal cell proliferation in an injured blood vessel of a subject comprising administering to the blood vessel a replication-deficient recombinant adenovirus which functionally encodes a DNA which can decrease the proliferation of neointimal cells, such that the adenovirus remains at the site of injury for a time sufficient for the adenovirus to selectively infect and express the DNA in neointimal cells, thereby preventing the proliferation of neointimal cells. By "preventing neointimal cell proliferation" is meant that proliferation is decreased and can include sufficiently decreased as to constitute inhibition of proliferation. This method can be used to treat any condition in which injury to a blood vessel causes neointimal formation, such as primary atherosclerosis.

The initial amount of adenovirus necessary to deliver a therapeutic or prophylactic amount of DNA to human neointimal cells can be deduced from the rat data set forth herein and from similar experiments utilizing adenovirus for gene therapy for other pathologies. The dose can then be optimized using standard techniques.

The invention also provides a method of screening DNA for the ability to inhibit proliferation of or to have cytotoxic effects on neointimal cells comprising administering to an injured blood vessel in a subject at the site of injury a replication-deficient adenovirus which functionally encodes the DNA, for a time sufficient for the adenovirus to selectively infect neointimal cells; and detecting inhibition of proliferation of or toxicity to the neointimal cells, such inhibition or toxicity indicating a DNA having the ability to inhibit proliferation of or to have cytotoxic effects on neointimal cells. Inhibition of proliferation of or toxicity to neointimal cells can be detected by any of several known methods, such as described herein. Naturally, such screening would preferably be performed in a non-human animal.

While adenovirus are utilized herein, the invention also contemplates the use of other viral vectors, so long as these vectors can selectively infect neointimal cells and selectively express the DNA encoded by the viral vector. Such vectors can be screened for utility using the methods taught herein.

The present invention is more particularly described in the following examples which are intended as illustrative only since numerous modifications and variations therein will be apparent to those skilled in the art.

EXAMPLES

Adenovirnus Vectors. The replication deficient recombinant adenovirus (Ad.RSVβgal) has previously been described (28,33). Briefly, the recombinant virus encodes for the histochemical marker gene β-galactosidase (β-gal). The gene, derived from $E.\ coli$, has been modified by a eukaryotic nuclear translocation signal and placed under the control of the Rous Sarcoma Virus (RSV) long terminal repeat. Expression of the β-gal gene product results in a nuclear dominant blue staining pattern when cells are exposed to the chromogen 5-bromo4-chloro-3 indoyl β-D-galactopyranoside (X-gal). A similar adenovirus containing the human cystic fibrosis transmembrane conductance regulator cDNA (AdCFTR) (29), whose recombinant gene product does not react with the X-gal chromogen, was used as a control. Viral stocks ($1.5 \times 10^{10}$ pfu/ml) were prepared by passaging recombinant adenovirus in 293 cells. (31, 39)

Cell Culture. Vascular SMCs were isolated from a rat thoracic aorta by enzymatic digestion as previously described (40). Cells were maintained in M199 medium (Biofluids, Gaithersburg, Md.) containing 10% FBS (Biofluids, Gaithersburg, Md.) and 1X penicillin/ streptomycin in humidified air containing 5% $CO_2$ at 37° C. Cells were routinely passaged just before reaching confluence by brief exposure to Puck's saline solutions containing 0.25 mg/ml trypsin (Biofluids, Gaithersburg, Md.) and 0.5 mM EDTA. At passage 3, cells were placed on 8 well microchamber slides and stained for alpha smooth muscle actin (Sigma Immunochemicals, Co., St. Louis, Mo.) to confirm their identity.

In Vitro Gene Transfer. Early passage (P4) SMCs were plated in duplicate on T-25 culture flasks and grown to 30% confluence. They were then placed in media containing 0.5% serum and allowed to become quiescent over 36 hrs. The cells were then washed twice in phosphate buffered saline (PBS) and incubated for 5, 15, 30, 60 or 120 min in 2 ml of media containing $2.5 \times 10^7$ pfu/ml, which was equivalent to approximately 100 pfu of Ad.RSVβgal per cell. After the given interval, the cells were washed five times in PBS and incubated in 5 ml of media containing 0.5% serum for 24 hrs. Prior to staining in X-gal solution, cells were washed and fixed for 5 min in 2% formaldehyde and 0.2% glutaraldehyde in PBS pH 7.4. The percent of transfected cells was calculated by counting 500 cells in each of two duplicate flasks and noting the number of cells with nuclear dominant blue staining. Percentages represent an average for 2 flasks at each time point.

Animals. All animals were studied under protocols approved by the Animal Care and Use Committee of the National Heart, Lung, and Blood Institute and in accordance with the *Guide for the Care and Use of Laboratory Animals* (Department of Health and Human Services publication No. [NIH] 86-23, revised 1985).

A total of 33 adult Sprague-Dawley rats weighing 350–450 g (Taconic farms, Germantown, N.Y.) were used for these experiments. All procedures were performed under general anesthesia and using sterile technique. General anesthesia was administered using ketamine 150 mg/kg and xylazine 15 mg/kg IM and supplemental ketamine/xylazine IP as necessary. Beef lung heparin (Upjohn, Kalamazoo, Mich.) was routinely given IV (100 u/kg) prior to cross clamping the vessel for virus incubation. All viral incubations consisted of instilling a solution containing 0.5–1.0× $10^9$ pfu of adenovirus in a total volume of 100 μl for 45 minutes. Medium M199 (Biofluids, Gaithersburg, Md.) was used to dilute stock viral solution to the appropriate concentration. Upon completion of each procedure, animals were allowed to recover with free access to food and water.

In Vivo Gene Transfer Into Arterial Segments. Adenoviral-mediated gene transfer was first evaluated in uninjured arterial segments (n=4). In each rat the left carotid artery was exposed, proximal and distal control obtained, and an arteriotomy was made in the external carotid. A solution containing either Ad.RSVβgal or AdCFTR was instilled through the external carotid using a 24 g catheter (Criticon Inc., Tampa, Fla.). The solution was then evacuated, the external carotid was ligated, and the incision was closed. All rats in this group were sacrificed at 3 days after infection and the carotid was subsequently harvested, fixed and stained as described below.

To assess gene transfer to areas of vascular injury, i.e., including areas of neointimal cell formation, the left carotid artery of 29 rats was exposed and injured as previously described (41, 42). Briefly, the common carotid and its external branch were exposed and encircled using 4-0silk ties. An arteriotomy was then made in the external carotid artery and a 2F Fogarty embolectomy catheter was passed into the common carotid, filled with 0.2 cc of air and passed back and forth 3 times. The carotid artery of one group of rats (n=7) was exposed to virus immediately after injury. Adenoviral solution was delivered into the common carotid lumen via the external carotid artery. After the 45 minute incubation, the external carotid was ligated, the carotid reperfused, and the animal was allowed to recover as previously described.

In three other groups of animals, the arteries were exposed to virus either 3 (n=9), 7 (n=9) or 12 (n=4) days following injury. These animals were re-anesthetized following the prescribed time interval after injury. The common carotid was exposed through the previous incision and a portion of the common carotid measuring approximately 13 cm was isolated between 1 mm microvascular clamps. An arteriotomy was made in the common carotid using a 24 g catheter and the vessel was irrigated with 50–100 μl of normal saline. Adenoviral solution containing Ad.RSVβgal or control virus was delivered directly into the carotid lumen. At the conclusion of the viral incubation, the catheter was removed and the arteriotomy was closed using 3 interrupted 10-0 ethilon stitches (Ethicon Inc., Somerville, N.J.). The incision was closed and the animal was allowed to recover as described above.

Evaluation of In Vivo Gene Transfer. In 30 animals, gene transfer was routinely assessed three days after exposure to adenovirus. One group of animals in (n=3) which underwent infection 7 days after injury, were sacrificed two weeks after infection to determine persistence of gene expression. Animals were sacrificed by overdosing with pentobarbital.

The carotid artery was harvested and cut longitudinally to expose the lumen. It was then washed in 2 ml of PBS and fixed for 5 min in a solution containing 2% formaldehyde and 0.2% glutaraldehyde in PBS. The artery was washed in PBS several times to remove any excess fixative and placed into X-gal solution (5 mM $K_4Fe(CN)_6$, 5mM $K_3Fe(CN)_6$, 1 mM $MgCl_2$, and 1 mg/ml X-gal in PBS) for 4 hrs. For histologic examination, carotid arteries were cut into 2 mm segments, embedded in paraffin, cut into 5 $\mu$m sections, and counterstained with nuclear fast red. In order to estimate gene transfer efficiency in histologic sections, neointimal cells were counted in at least 3 high power (400×) fields from 3 or more histologic sections of each test artery and the percentage of nuclear dominant blue cells was calculated. At least 300 cells were counted in each section.

In two separate sections containing neointima, immunohistochemical staining with an antibody to alpha smooth muscle actin was performed. This analysis demonstrated cytoplasmic staining of most neointimal cells and medial smooth muscle cells, a finding in agreement with previous studies that identified neointimal cells as being primarily of SMC origin (41). In three of the animals that were infected three days after injury and sacrificed 3 days later, the brain, heart, and liver were also harvested to determine if gene expression in distal organs was detectable. These specimens were washed in PBS, fixed in 2% formaldehyde, 0.2% glutaraldehyde for 20 minutes and stained in X-gal solution for 6 hrs. Histologic sections were counterstained using nuclear fast red.

RESULTS

In Vitro Gene Transfer. We first sought to assess the efficiency of adenoviral mediated gene transfer in cultured primary rat aortic SMCs. $\beta$-gal expression was detected in approximately 25% of the SMCs after a 5 min exposure to adenovirus. With increasing time of incubation, a higher percentage of cells stained positive (FIG. 1). With a 1 hr exposure, close to 70% of cells appeared positive. As expected, the predominant staining was intranuclear, since the $\beta$-gal gene was modified by the addition of a nuclear localizing sequence. A nuclear dominant blue stain was not seen in mock infected cells. As noted by others (21, 24), however, we noted occasional faint blue cytoplasmic staining in both infected and control cells of vascular origin. Although these results were obtained on quiescent cells, qualitatively similar results were obtained in cells maintained in normal growth media (data not shown).

In Vivo Gene Transfer Into Uninjured Arterial Segments. Extrapolating from our in vitro data, we chose to expose the vessel wall to adenoviral solution for 45 min. With this incubation period, transfection efficiency appeared to be within the plateau region of the in vitro data curve (FIG. 1). $\beta$-gal gene expression in uninjured arterial segments (n=2) could be detected on gross examination when assessed three days after infection. Histological examination showed $\beta$-gal staining of scattered endothelial cells throughout the region incubated with adenovirus. Staining was also occasionally noted in cells of the adventitia. No medial SMCs stained for $\beta$-galactosidase activity. This suggests that the endothelium or the internal elastic lamina may form a barrier to adenoviral infection of medial cells. We observed no $\beta$-gal staining in arteries infected with the AdCFTR control virus (n=2).

In Vivo Gene Transfer Into Arterial Segments. In order to assess the efficiency of gene transfer in injured arterial segments, and to determine whether neointimal cells have different susceptibility to gene transfer than medial SMCs, the rat carotid injury model was used. In this model, balloon abrasion removes the endothelial layer and disrupts one or more layers of internal elastic lamina (41). The injury activates medial SMCs, which begin to migrate and proliferate to form a neointima between 3 and 5 days after injury. A well formed neointima is routinely present at 12 days after injury. For this reason we assessed gene transfer immediately, 3 days, 7 days and 12 days after balloon injury.

In carotid segments where virus was instilled immediately after injury, only 3 of 5 segments showed gross evidence of $\beta$-gal expression. The staining was, in general, limited to less than 5% of the vessel surface. Histological examination confirmed that no endothelial layer existed. Despite this, only occasional medial SMCs positively stained for $\beta$-gal (data not shown). Similar results were obtained when infection was delayed to 3 days after injury. In this group only 4 of 7 carotid vessels incubated with Ad.RSV$\beta$gal showed gross evidence of $\beta$-gal staining. This was again limited to less than 5% of the vessel surface. Histology revealed only occasional neointimal or medial SMC staining. Control segments treated with AdCFTR either immediately (n=2) or 3 days after injury (n=2) showed no staining for $\beta$-gal activity.

In contrast, markedly increased $\beta$-gal activity was observed in segments in which infection was delayed until 7 days after injury. At this time, we found that neointima covered most, but not all of the arterial surface. Intense staining, indicative of gene transfer and expression, was evident on gross examination in each of the arterial segments obtained from these animals exposed to $\beta$-gal containing adenovirus. Histological examination showed staining limited almost exclusively to the neointima We examined multiple histologic sections containing neointima from each of the animals infected 7 days after injury. The efficiency of gene transfer was noted to vary from approximately 20% to over 75% of neointimal cells. In the majority of sections, over 50% of neointimal cells expressed $\beta$-gal. Surprisingly, neointimal cells were selectively targeted, as we observed that very few cells located deep to the first layer of internal elastic lamina stained positive for $\beta$-gal, whether or not overlying neointima was present. Arterial segments infected 7 days after injury with control AdCFTR virus (n=3) showed no visible staining on gross or microscopic examination.

In the final group in this series of experiments, we exposed arteries to Ad.RSV$\beta$gal at 12 days after injury and harvested the vessels 3 days later (n=2). At this point, the neointima is thicker and covers most of the arterial surface. Each of these segments showed uniform staining of the luminal surface. Histology again showed efficient gene transfer that was selective for neointimal cells. In general, the cells located in the more superficial portions of the neointima appeared to have a higher efficiency of gene transfer. Carotid segments in which animals were infected 12 days after injury with the control adenovirus AdCFTR showed no evidence of staining (n=2).

In the three animals in which distal organs (brain, liver, and heart) were harvested in order to evaluate gene expression at distal sites, no β-gal staining could be visualized in any area by gross or histologic evaluation.

Persistence of Gene Expression. In a separate group consisting of three animals, we made a preliminary assessment of the persistence of gene expression. Rats were infected seven days after injury and their carotid arteries were harvested two weeks later. Analysis of β-gal expression in these segments showed persistence of β-gal activity in each of the three animals. However, relative to segments harvested 3 days after infection, expression was qualitatively diminished.

Transfer thymidine kinase gene to treat restenosis. The published gene which encodes for herpes virus thymidine kinase was transferred into injured rat arterial segments. The premise of this experiment was that if this gene was efficiently transferred into neointima, then we should be able to inhibit further neointimal development by treatment with the nucleoside analogue Ganciclovir. Treatment by Ganciclovir of rats not infected by thymidine kinase-containing adenoviral vectors should allow normal, uninhibited neointimal development.

The results of these studies confirmed this hypothesis, i.e., we have been able to inhibit restenosis by using adenovirus vectors. Our protocol involves performing a standard rat carotid injury, as described above. This is followed by infection by the method described above with an adenovirus vector containing the herpes virus thymidine kinase gene, inserted by the method described herein, at one week after injury. Rats are then treated with Ganciclovir, twice daily, for two weeks. The arterial segments are then harvested and analyzed for neointimal development. Three other groups of rats were used as controls. These involved rats which were infected with adenoviruses which did not contain the thymidine kinase gene and rats which were treated with saline. Data are expressed below in Table I as a ratio of neointima to media. A higher ratio indicates a worse or more significant neointimal development.

TABLE I

| Groups | Ratio |
| --- | --- |
| Thymidine kinase virus with saline | 1.33 |
| Control virus with saline | 1.31 |
| Control virus with Ganciclovir | 1.05 |
| Thymidine kinase virus w/Ganciclovir | 0.65 |

In the data presented above for β-gal expression, in uninjured vessels, gene transfer and expression were confined predominantly to endothelial cells and adventitial cells. Only rare medial SMCs expressed the β-gal gene product. Adventitial staining was often found around the vasa vasorum, which suggests the virus may have entered the vasa vasorum and thereby gained access to, and infected, the surrounding cells. Another possibility is that minute quantities of viral solution could have been inadvertently spilled on the adventitial surface during the procedure. The efficiency of staining in uninjured vessels appeared to be considerably less impressive than was previously seen in sheep carotid segments (36).

In injured vessels, we noted a marked difference in gene transfer efficiencies depending upon when after injury the artery was exposed to virus. At early time points after injury (3 days or less), when endothelial cells were absent and there were few neointimal cells, efficiency of gene transfer was low and expression was confined to scattered medial and neointimal cells. Exposing vessels to adenovirus 7 days or 12 days after injury, during which time significant neointima had formed, we found a markedly increased efficiency of β-gal gene transfer and expression. Surprisingly, however, most of the cells expressing the β-gal gene product were located on the luminal surface of the internal elastic lamina; i.e., the transfected cells were almost exclusively neointimal cells.

The mechanism responsible for this difference in susceptibility between neointimal and medial SMCs to adenoviral-mediated gene transfer and expression is unclear. While not limiting this invention, the most probable explanation is that a physical barrier, most likely the internal elastic lamina, prevents diffusion of virus into medial layers. Thus, neointimal cells, which reside on the luminal side of the internal elastic lamina are able to be infected, while medial SMCs, which reside deep to the internal elastic lamina, are not. Alternatively, the process of injury induced neointimal proliferation may affect the expression of the as yet uncharacterized adenoviral cell surface receptor. Increased expression of the target viral receptor by proliferating neointimal cells could explain their efficient and selective uptake of adenovirus. Of note, however, in our in vitro experiments, we found no appreciable difference in adenoviral transduction between quiescent and proliferating SMCs.

In this study, we routinely evaluated gene expression 3 days after infection. In 3 segments, however, we assessed β-gal staining 2 weeks after infection. These segments showed continued, but diminished, expression of the marker gene. Previous studies in endothelial cells in vitro have shown that gene expression peaks around 7 days after infection and persists for at least 14 days (43). The same is true in endothelial cells in vivo (36). Long-term gene expression would not be expected from adenoviral gene transfer, since the virus does not stably integrate into the genome of the host cell. Such a time frame of gene expression, while a potential drawback in the treatment of inherited genetic disease, can be an advantage for the treatment of a temporally discrete event such as restenosis. Any treatment strategy that uses recombinant adenovirus must address the question of safety. The general lack of stable integration of adenovirus, as opposed to retroviruses, is a significant advantage in that issues of insertional mutagenesis are of less concern (37). The safety of adenovirus in humans has been tested in vaccine trials in the past (44–47) and presently in ongoing clinical trials in the treatment of cystic fibrosis (48). Although we made no concerted effort to evaluate distal organs in all animals exposed to Ad.RSVβgal, we could not detect β-gal expression in the brain, liver, or heart of each of 3 animals in which these organs were harvested. This demonstrates that adenoviral gene transfer can in large part be limited to discrete vascular segments without subjecting distal organs to infection.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES

1. Leimgruber, P. P. et al., "Restenosis after Successful Coronary Angioplasty in Patients with Single Vessel Disease," *Circulation*, 73:710–717 (1986).

2. Gruentzig, A. R. et al., "Long-term Follow up After PTCA: The Early Zurich Experience," *N. Engl. J. Med.*, 316:1127–1132 (1987)
3. Val, P. G. et al., "The Montreal Heart Institute.
4. Nobuyoshi, M. et al., "Restenosis After Successful Percutaneous Transluminal Coronary Angioplasty; Serial Angiographic Follow-up of 220 Patients," *Jour. Am. Coll. Cardiol.*, 12:616–623 (1988).
5. Serruys, P. W. et al., "Incidence of Restenosis After Successful Coronary Angioplasty: A Time Related Phenomenon. A Quantitative Angiographic Study in 342 Consecutive Patients at 1, 2 and 3 Months," *Circulation*, 77:361–372 (1988).
6. Liu, M. W. et al., "Restenosis After Coronary Angioplasty: Potential Biologic Determinants and Role of Intimal Hyperplasia," *Circulation*, 79:1374–1386 (1989).
7. Forrester, J. S. et al., "A Paradigm for Restenosis Based on Cell Biology: Clues for the Development of New Preventive Therapies," *Jour. Am. Coll. Cardiol.*, 17:758–769 (1991).
8. Ip, J. H. et al., "The role of Platelets thrombin and Hyperplasia in Restenosis After Coronary Angioplasty," *Jour. Am. Coll. Cardiol.*, 17:77B–88B (1991).
9. Schwartz, R. S. et al., "The Restenosis Paradigm Revisited: An Alternative Proposal for Cellular Mechanisms," *Jour. Am. Coll. Cardiol.*, 20(5):1284–1293 (1992).
10. Ferns, G. A. A. et al., "Inhibition of Neointimal Smooth Muscle Accumulation After Angioplasty by an Antibody to PDGF," *Science*, 253:1129–1132 (1991).
11. Lindner, V. et al., "Proliferation of Smooth Muscle Cells After Vascular Injury is Inhibited by an Antibody Against Basic Fibroblast Growth Factor," *Proc. Natl. Acad. Sci. USA.*, 88:3739–3743 (1991).
12. Epstein, S. E. et al., "Cytotoxic Effects of a Recombinant Chimeric Toxin on Rapidly Proliferating Vascular Smooth Muscle Cells," *Circulation*, 84:778–787 (1991)
13. Simons, M. et al., "Antisense c-myb Oligonucleotides Inhibit Intimal Arterial Smooth Muscle Cell Accumulation in vivo," *Nature*, 83:2007–2011 (1991).
14. Simons, M. et al., "In Vitro Effects of a Recombinant Toxin Targeted to the FGF Receptor on Rat Vascular Smooth Muscle and Endothelial Cells," *Circ. Res.*, 71:640–645 (1992).
15. Casscells, W. et al., "Elimination of Smooth Muscle Cells in Experimental Restenosis: Targeting of Fibroblast Growth Factor Receptors," *Proc. natl. Acad. Sci. U.S.A.*, 89:7159–7163 (1992).
16. Speir E., et al., "Inhibition of Smooth Muscle Cell Proliferation by an Antisense Oligodeoxynucleotide Targeting the mRNA Encoding PCNA," *Circulation*, 86:538–547 (1992).
17. Pickering, G. et al., "Inhibition of Proliferation of Human Vascular Smooth Muscle Cells Using Antisense Oligonucleotides to PCNA (abst)." *Jour. Am. Coll. Cardiol.*, 19:165A (1992).
18. Simons, M. et al., "Antisense Nonmuscle Myosin Heavy Chain and C-myb Oligonucleotides Suppress Smooth Muscle Cell Proliferation In Vitro, *Circ. Res.*, 70:835–843 (1992).
19. Biro, S. et al., "Inhibitory Effects of Antisense Oligodeoxynucleotides Targeting c-myc mRNA on Smooth Muscle Cell Proliferation and Migration," *Proc. Natl. Acad. Sci., USA*, 90:654–658 (1993).
20. Nabel, E. G. et al., "Site-specific Gene Expression In Vivo by Direct Gene Transfer Into the Arterial Wall," *Science*, 249:1285–1288 (1990).
21. Lim, C. S. et al., "Direct In Vivo Gene Transfer Into the Coronary and Peripheral Vasculatures of the Intact Dog," *Circulation*, 83:2007–2011 (1991).
22. Chapman, G. D. et al., "Gene Transfer Into Coronary Arteries of Intact Animals With a Percutaneous Balloon Catheter," *Circ. Res.*, 71:27–33 (1992).
23. Leclerc, G. et al., "Percutaneous Arterial Gene Transfer in a Rabbit Model: Efficiency in Normal and Balloon-Dilated Atherosclerotic Arteries," *J. Clin. Invest.*, 90:936–944 (1992).
24. Flugelman, M. Y. et al., "Low Level In Vivo Gene Transfer Into the Arterial Wall Through a Perforated Balloon Catheter," *Circulation*, 85:1110–1117 (1992).
25. Stratford-Perricaudet, L. D. et al., "Evaluation of the Transfer and Expression in Mice of an Enzyme-Encoding Gene Using a Human Adenovirus Vector," *Hum. Gene Ther.*, 1:241–256 (1990).
26. Rosenfeld, M. A. et al., "Adenovirus-Mediated Transfer of a Recombinant αI-Antitrypsin Gene to the Lung Epithelium In Vivo, *Science*, 252:431–434 (1991).
27. Quantin, B. et al., "Adenovirus as an Expression Vector in Muscle Cells In Vivo," *Proc. Natl. Acad. Sci. U S A*, 89:2581–2584 (1992).
28. Stratford-Perricaudet, L. D. et al., "Widespread Long-Term Gene Transfer to Mouse Skeletal Muscles and Heart," *J. Clin. Invest.*, 90:626–630 (1992).
29. Rosenfeld, M. A. et al., "In Vivo Transfer of the Human Cystic Fibrosis Transmembrane Conductance Regulator Gene to the Airway Epithelium," *Cell*, 68:143–155 (1992).
30. Jaffe, H. A. et al., "Adenovirus-Mediated In Vivo Gene Transfer and Expression in Normal Rat Liver," *Nature Genet.*, 1:372–378 (1992).
31. Mastrangeh, A. et al., "Diversity of Airway Epithelial Cell Targets for In Vivo Recombinant Adenovirus-Mediated Gene Transfer," *J. Clin. Invest.*, 91:225–234 (1993).
32. Ragot, T. et al., "Efficient Adenovirus-Mediated Transfer of a Human Minidystrophin Gene to Skeletal Muscle of MDX Mice," *Nature*, 361:647–650(1993).
33. Bajocchi, G. et al., "Direct In Vivo Gene Transfer to Ependymal Cells in the Central Nervous System Using Recombinant Adenovirus Vectors," *Nature Genet.*, 3:229–234 (1993).
34. Davidson, B. L. et al., "A Model System for In Vivo Gene Transfer Into the Central Nervous System Using an Adenoviral Vector," *Nature Genet.*, 3:219–223 (1993).
35. Akli, S. et al., "Transfer of a Foreign Gene Into the Brain Using Adenovirus Vectors," *Nature Genet.*, 3:224–228 (1993).
36. Lemarchand, P. et al., "In Vivo Gene Transfer and Expression in Normal, Uninjured Vessels Using Replication Deficient Recombinant Adenovirus Vectors," *Circ. Res.*, (In Press) (1993).
37. Berkner, K. L. et al., "Expression of Heterologous Sequences in Adenoviral Vectors, in *Current Topics in Microbiology and Immunology*, berlin-Heidelberg, Springer-Verlag, pp. 39–66 (1992).
38. Miller, D. G. et al., "Gene Transfer by Retrovirus Vectors Occurs Only in Cells that are Actively Replicating at the Time of Infection," *Mol. Cell Biol.*, 10(8):4239–4242 (1990).
39. Graham, F. L. et al., "A New Technique for the Assay of Infectivity of Human Adenovirus 5 DNA," *Virology*, 52:456–467 (1973).
40. Campbell, R. H. et al., "Methods of Growing Vascular Smooth Muscle in Culture, in Campbell J. H., Campbell, G. R. (eds): *Vascular Smooth Muscle in Culture*, Boca Raton, Fla., CRC Press, Inc., pp. 15–22 (1987).
41. Clowes, A. W. et al., "Kinetics of Cellular Proliferation After Arterial Injury: I. Smooth Muscle Growth in the Absence of Endothelium," *Lab. Invest.*, 49(3):327–333 (1983).

42. Clowes, A. W. et al., "Mechanisms of Stenosis After Arterial Injury," Lab Invest., 49(2):208 –215 (1983).
43. Lemarchand, P. et al., "Adenovirus-Mediated Transfer of a Recombinant Human αl-Antitrypsin cDNA to Human Endothelial Cells, Proc. Natl. Acad. Sci. USA, 89:6482–6486 (1992).
44. Dudding, B. A. et al., "Enteric Immunization with Live Adenovirus Type 21 Vaccine. I. Tests for Safety, Infectivity, Immunogenicity, and Potency in Volunteers," Infect. Immun., 5:295–299 (1972).
45. Takafuji, E. T. et al., "Simultaneous Administration of Live, Enteric-Coated Adenovirus Types 4, 7 and 21 Vaccines: Safety and Immunogenicity," J. Infect. Dis., 140:48–53 (1979).
46. "Potential Use of Live Viral and Bacterial Vectors for Vaccines," WHO Meeting, Geneva, June 19–22, 1989, Vaccine, 8:425–437 (1990).
47. Tacket C. O., et al., "Initial Safety and Immunogenicity Studies of an Oral Recombinant Adenohepatitis B Vaccine," Vaccine, 10:673–676 (1992).
48. Crystal, R. G. et al., Gene Therapy of the Respiratory Manifestations of Cystic Fibrosis Using a Replication Deficient, Recombinant Adenovirus to Transfer the Normal Human Cystic Fibrosis Transmembrane Conductance Regulator cDNA to the Airway Epithelium, Bethesda, Md. 20892, NIH Office of Recombinant DNA Activities, NIH 31/4B11, (1992).
49. McGrory, W. J. et al., "A Simple Technique for the Rescue of Early Region 1 Mutations into Infectious Human Adenovirus," (1988).
50. J. of Coronary Artery Disease, 4:469–475 (1993)

What is claimed is:

1. A method of selectively expressing DNA in neointimal cells in an injured blood vessel of a subject comprising administering a replication-deficient recombinant adenovirus, which functionally encodes the DNA, to the blood vessel at the site of injury, such that the adenovirus remains at the site of injury for a time sufficient for the adenovirus to selectively infect neointimal cells and thereby selectively express the DNA in neointimal cells.

2. The method of claim 1, wherein the administration step is performed at least about 4 days after the blood vessel is injured.

3. The method of claim 1, wherein the administration step is performed at least about 7 days after the blood vessel is injured.

4. The method of claim 1, wherein the administration step is performed at least about 12 days after the blood vessel is injured.

5. The method of claim 1, wherein the time the adenovirus remains at the site of injury is from about 15 minutes to about 60 minutes.

6. The method of claim 1, wherein the DNA encodes a protein.

7. The method of claim 1, wherein the DNA encodes an antisense ribonucleic acid.

8. A method of treating restenosis in an injured blood vessel of a subject comprising administering to the blood vessel a replication-deficient recombinant adenovirus which functionally encodes a DNA which can decrease the proliferation of neointimal cells, such that the adenovirus remains at the site of injury for a time sufficient for the adenovirus to selectively infect and express the DNA in neointimal cells, thereby decreasing or inhibiting the proliferation of neointimal cells and treating restenosis.

9. The method of claim 8, wherein the administration step is performed at least about 4 days after the blood vessel is injured.

10. The method of claim 8, wherein the DNA encodes a protein.

11. The method of claim 8, wherein the DNA encodes an antisense ribonucleic acid.

12. The method of claim 10, wherein the protein is selected from the group consisting of herpes simplex thymidine kinase, dominant negative ras gene product and nitric oxide synthase.

13. The method of claim 11, wherein the antisense ribonucleic acid is derived from the group consisting of c-myc, c-myb, CDC2 and PCNA.

14. The method of claim 8, wherein the DNA is cytotoxic to the neointimal cells.

15. A method of decreasing neointimal cell proliferation in an injured blood vessel of a subject comprising administering to the blood vessel a replication-deficient recombinant adenovirus which functionally encodes a DNA which can decrease the proliferation of neointimal cells, such that the adenovirus remains at the site of injury for a time sufficient for the adenovirus to selectively infect and express the DNA in neointimal cells, thereby decreasing the proliferation of neointimal cells.

16. A method of screening DNA for the ability to inhibit or decrease proliferation of or to have cytotoxic effects on neointimal cells comprising:

administering to an injured blood vessel in a subject at the site of injury a replication-deficient adenovirus which functionally encodes the DNA, for a time sufficient for the adenovirus to selectively infect neointimal cells; and detecting inhibition or decrease of proliferation of or toxicity to the neointimal cells, such inhibition, decrease or toxicity indicating a DNA having the ability to inhibit or decrease proliferation of or to have cytotoxic effects on neointimal cells.

17. A method of reducing neointimal cell proliferation in an injured blood vessel of a subject comprising administering to the blood vessel (1) a replication-deficient recombinant adenovirus which functionally encodes herpes simplex virus thymidine kinase, such that the adenovirus remains at the site of injury for a time sufficient for the adenovirus to selectively infect neointimal cells, and (2) an effective amount of ganciclovir, thereby reducing the proliferation of neointimal cells.

18. The method of claim 17, wherein the replication-deficient recombinant adenovirus is administered at any point within about 1 day prior to injury to about 15 days after injury to the blood vessel.

19. The method of claim 18, wherein the replication-deficient recombinant adenovirus is administered at any point within about 0 to about 7 days after injury to the blood vessel.

20. The method of claim 18, wherein the ganciclovir is administered in a series of individual doses.

* * * * *